(12) United States Patent
Schreck

(10) Patent No.: US 8,349,000 B2
(45) Date of Patent: *Jan. 8, 2013

(54) MINIMALLY-INVASIVE HEART VALVES

(75) Inventor: Stefan Schreck, Vista, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 311 days.

This patent is subject to a terminal disclaimer.

(21) Appl. No.: 12/767,278

(22) Filed: Apr. 26, 2010

(65) Prior Publication Data

US 2010/0211165 A1 Aug. 19, 2010

Related U.S. Application Data

(60) Continuation of application No. 12/099,566, filed on Apr. 8, 2008, now Pat. No. 8,092,518, which is a continuation of application No. 10/766,139, filed on Jan. 28, 2004, now Pat. No. 7,381,218, which is a continuation of application No. 10/185,812, filed on Jun. 28, 2002, now Pat. No. 6,767,362, which is a division of application No. 09/549,413, filed on Apr. 6, 2000, now Pat. No. 6,454,799.

(51) Int. Cl.
*A61F 2/24* (2006.01)

(52) U.S. Cl. ........................ 623/2.18; 623/2.14

(58) Field of Classification Search ................ 623/1.24, 623/1.26, 2.12–2.19, 900
See application file for complete search history.

(56) References Cited

U.S. PATENT DOCUMENTS 3,409,013 A 11/1968 Berry
3,472,230 A 10/1969 Fogarty et al.
(Continued)

FOREIGN PATENT DOCUMENTS

DE 2246526 3/1973
(Continued)

OTHER PUBLICATIONS

Andersen, et al., "Transluminal implantation of artificial heart valves. Description of a new expandable aortic valve and initial results with implantation by catheter technique in closed chest pigs." European Heart Journal (1992), 13, 704-708.

(Continued)

*Primary Examiner* — Thomas J Sweet
*Assistant Examiner* — Cheryl Miller
(74) *Attorney, Agent, or Firm* — David L. Hauser; Pui Tong Ho

(57) ABSTRACT

Expandable prosthetic heart valves for minimally invasive valve replacement are disclosed. In one preferred embodiment, an expandable prosthetic heart valve includes a support stent comprising an expandable tubular base along an inflow end and three upstanding commissure posts along an outflow end. The three commissure posts are spaced at 120 degree intervals with gaps therebetween. The prosthetic heart valve further includes a tubular flexible member having a prosthetic section and a fabric section. The prosthetic section is connected to the three commissure posts and defines three leaflets, preferably formed of pericardial tissue. The fabric section is sutured to the expandable tubular base. The tubular base may be formed with a shape memory material and is sized for deployment with an annulus of a native aortic valve. After deployment, the three commissure posts support the leaflets above the tubular base for replacing the function of the native aortic valve. In one variation, flanges may be provided on the support stent for improving attachment of the support stent to the host tissue.

14 Claims, 10 Drawing Sheets

U.S. PATENT DOCUMENTS

| | | | |
|---|---|---|---|
| 3,548,417 A | 12/1970 | Kisher | |
| 3,587,115 A | 6/1971 | Shiley | |
| 3,657,744 A | 4/1972 | Ersek | |
| 3,671,979 A | 6/1972 | Moulopoulos | |
| 3,714,671 A | 2/1973 | Edwards et al. | |
| 3,755,823 A | 9/1973 | Hancock | |
| 4,035,849 A | 7/1977 | Angell et al. | |
| 4,056,854 A | 11/1977 | Boretos et al. | |
| 4,106,129 A * | 8/1978 | Carpentier et al. | 623/2.18 |
| 4,222,126 A | 9/1980 | Boretos et al. | |
| 4,265,694 A | 5/1981 | Boretos et al. | |
| 4,297,749 A | 11/1981 | Davis et al. | |
| 4,339,831 A | 7/1982 | Johnson | |
| 4,343,048 A | 8/1982 | Ross et al. | |
| 4,345,340 A | 8/1982 | Rosen | |
| 4,373,216 A | 2/1983 | Klawitter | |
| 4,406,022 A | 9/1983 | Roy | |
| 4,470,157 A | 9/1984 | Love | |
| 4,501,030 A * | 2/1985 | Lane | 623/2.18 |
| 4,535,483 A | 8/1985 | Klawitter et al. | |
| 4,574,803 A | 3/1986 | Storz | |
| 4,592,340 A | 6/1986 | Boyles | |
| 4,605,407 A | 8/1986 | Black et al. | |
| 4,612,011 A | 9/1986 | Kautzky | |
| 4,643,732 A | 2/1987 | Pietsch et al. | |
| 4,655,771 A | 4/1987 | Wallsten | |
| 4,692,164 A | 9/1987 | Dzemeshkevich et al. | |
| 4,733,665 A | 3/1988 | Palmaz | |
| 4,759,758 A | 7/1988 | Gabbay | |
| 4,762,128 A | 8/1988 | Rosenbluth | |
| 4,777,951 A | 10/1988 | Cribier et al. | |
| 4,787,899 A | 11/1988 | Lazarus | |
| 4,787,901 A | 11/1988 | Baykut | |
| 4,796,629 A | 1/1989 | Grayzel | |
| 4,829,990 A | 5/1989 | Thuroff et al. | |
| 4,851,001 A | 7/1989 | Taheri | |
| 4,856,516 A | 8/1989 | Hillstead | |
| 4,878,495 A | 11/1989 | Grayzel | |
| 4,878,906 A | 11/1989 | Lindemann et al. | |
| 4,883,458 A | 11/1989 | Shiber | |
| 4,922,905 A | 5/1990 | Strecker | |
| 4,966,604 A | 10/1990 | Reiss | |
| 4,979,939 A | 12/1990 | Shiber | |
| 4,986,830 A | 1/1991 | Owens et al. | |
| 4,994,077 A | 2/1991 | Dobben | |
| 5,007,896 A | 4/1991 | Shiber | |
| 5,026,366 A | 6/1991 | Leckrone | |
| 5,032,128 A | 7/1991 | Alonso | |
| 5,037,434 A | 8/1991 | Lane | |
| 5,047,041 A | 9/1991 | Sammuels | |
| 5,059,177 A | 10/1991 | Towne et al. | |
| 5,080,668 A | 1/1992 | Bolz et al. | |
| 5,085,635 A | 2/1992 | Cragg | |
| 5,089,015 A | 2/1992 | Ross | |
| 5,152,771 A | 10/1992 | Sabbaghian et al. | |
| 5,163,953 A * | 11/1992 | Vince | 623/2.11 |
| 5,167,628 A | 12/1992 | Boyles | |
| 5,192,297 A | 3/1993 | Hull | |
| 5,266,073 A | 11/1993 | Wall | |
| 5,282,847 A | 2/1994 | Trescony et al. | |
| 5,295,958 A | 3/1994 | Shturman | |
| 5,332,402 A | 7/1994 | Teitelbaum | |
| 5,360,444 A | 11/1994 | Kusuhara | |
| 5,370,685 A | 12/1994 | Stevens | |
| 5,397,351 A | 3/1995 | Pavcnik et al. | |
| 5,411,055 A | 5/1995 | Kane et al. | |
| 5,411,552 A | 5/1995 | Andersen et al. | |
| 5,443,446 A | 8/1995 | Shturman | |
| 5,480,424 A | 1/1996 | Cox | |
| 5,500,014 A | 3/1996 | Quijano et al. | |
| 5,545,209 A | 8/1996 | Roberts et al. | |
| 5,545,214 A | 8/1996 | Stevens | |
| 5,549,665 A | 8/1996 | Vesely | |
| 5,554,185 A | 9/1996 | Block et al. | |
| 5,571,175 A | 11/1996 | Vanney et al. | |
| 5,591,185 A | 1/1997 | Kilmer et al. | |
| 5,607,464 A | 3/1997 | Trescony et al. | |
| 5,609,626 A | 3/1997 | Quijano et al. | |
| 5,639,274 A | 6/1997 | Fischell et al. | |
| 5,665,115 A | 9/1997 | Cragg | |
| 5,716,417 A | 2/1998 | Girard et al. | |
| 5,728,068 A | 3/1998 | Leone et al. | |
| 5,749,890 A | 5/1998 | Shaknovich | |
| 5,756,476 A | 5/1998 | Epstein | |
| 5,769,812 A | 6/1998 | Stevens et al. | |
| 5,800,508 A | 9/1998 | Goicoechea et al. | |
| 5,840,081 A | 11/1998 | Andersen et al. | |
| 5,855,597 A | 1/1999 | Jayaraman | |
| 5,855,601 A | 1/1999 | Bessler | |
| 5,855,602 A | 1/1999 | Angell | |
| 5,925,063 A | 7/1999 | Khosravi | |
| 5,957,949 A * | 9/1999 | Leonhardt et al. | 623/1.24 |
| 6,027,525 A | 2/2000 | Suh et al. | |
| 6,132,473 A | 10/2000 | Williams et al. | |
| 6,168,614 B1 | 1/2001 | Andersen et al. | |
| 6,171,335 B1 | 1/2001 | Wheatley et al. | |
| 6,174,327 B1 | 1/2001 | Mertens et al. | |
| 6,210,408 B1 | 4/2001 | Chandrasakaran et al. | |
| 6,217,585 B1 | 4/2001 | Houser et al. | |
| 6,221,091 B1 | 4/2001 | Khosravi | |
| 6,231,602 B1 | 5/2001 | Carpentier et al. | |
| 6,245,102 B1 | 6/2001 | Jayaraman | |
| 6,299,637 B1 | 10/2001 | Shaolian | |
| 6,302,906 B1 | 10/2001 | Goecoechea et al. | |
| 6,309,417 B1 * | 10/2001 | Spence et al. | 623/2.11 |
| 6,338,740 B1 * | 1/2002 | Carpentier | 623/2.13 |
| 6,350,277 B1 | 2/2002 | Kocur | |
| 6,425,916 B1 * | 7/2002 | Garrison et al. | 623/2.11 |
| 6,440,164 B1 | 8/2002 | Di Matteo et al. | |
| 6,454,799 B1 * | 9/2002 | Schreck | 623/2.18 |
| 6,458,153 B1 | 10/2002 | Bailey et al. | |
| 6,558,418 B2 * | 5/2003 | Carpentier et al. | 623/2.14 |
| 6,569,196 B1 | 5/2003 | Vesely et al. | |
| 6,582,462 B1 | 6/2003 | Andersen et al. | |
| 6,605,112 B1 | 8/2003 | Moll | |
| 6,652,578 B2 | 11/2003 | Bailey et al. | |
| 6,908,481 B2 | 6/2005 | Cribier | |
| 7,585,321 B2 | 9/2009 | Cribier | |
| 7,618,446 B2 | 11/2009 | Andersen et al. | |
| 2002/0077698 A1 * | 6/2002 | Peredo | 623/2.13 |

FOREIGN PATENT DOCUMENTS

| | | |
|---|---|---|
| DE | 19532846 | 3/1997 |
| DE | 19546692 | 6/1997 |
| DE | 19857887 | 7/2000 |
| DE | 19907646 | 8/2000 |
| EP | 0103546 | 3/1984 |
| EP | 0144167 | 6/1985 |
| EP | 0597967 | 12/1994 |
| EP | 0592410 | 10/1995 |
| EP | 0850607 | 7/1998 |
| EP | 1057460 | 12/2000 |
| EP | 1088529 | 4/2001 |
| FR | 2788217 | 7/2007 |
| GB | 2056023 | 3/1981 |
| SU | 1271508 | 11/1986 |
| WO | WO 91/17720 | 11/1991 |
| WO | WO 92/17118 | 10/1992 |
| WO | WO 93/01768 | 2/1993 |
| WO | WO 97/24080 | 7/1997 |
| WO | WO 98/29057 | 7/1998 |
| WO | WO 99/33414 | 7/1999 |
| WO | WO 99/40964 | 8/1999 |
| WO | WO 99/47075 | 9/1999 |
| WO | WO 00/18333 | 4/2000 |
| WO | WO 00/41652 | 7/2000 |
| WO | WO 00/47139 | 8/2000 |
| WO | WO 01/35878 | 5/2001 |
| WO | WO 01/49213 | 7/2001 |
| WO | WO 01/54624 | 8/2001 |
| WO | WO 01/54625 | 8/2001 |
| WO | WO 01/62189 | 8/2001 |
| WO | WO 01/64137 | 9/2001 |
| WO | WO 01/76510 | 10/2001 |

OTHER PUBLICATIONS

Andersen, Henning Rud, "History of Percutaneous Aortic Valve Prosthesis," Herz 34 2009 Nr. 5, Urban & Vogel, pp. 343-346, Skejby University Hospital Department of Cardiology, Aarhus, Denmark.

Almagor, M.D., Yaron, et al., "Balloon Expandable Stent Implantation in Stenotic Right Heart Valved Conduits," Journal of the American College of Cardiology, vol. 16, No. 6, pp. 1310-1314, Nov. 1, 1990; ISSN 0735-1097.

Sabbah, Ph.D., Hani N., et al., "Mechanical Factors in the Degeneration of Porcine Bioprosthetic Valves: An Overview," Journal of Cardiac Surgery, vol. 4, No. 4, pp. 302-309, Dec. 1989; ISSN 0886-0440.

Serruys, P.W., et al., "Stenting of Coronary Arteries. Are we the Sorcerer's Apprentice?," European Heart Journal (1989) 10, 774-782, pp. 37-45, Jun. 13, 1989.

Urban, M.D., Philip, "Coronary Artery Stenting," Editions Médecine et Hygiène, Genève, 1991, pp. 5-47.

Wheatley, M.D., David J., "Valve Prostheses," Rob & Smith's Operative Surgery, Fourth Edition, pp. 415-424, Butterworths 1986.

Benchimol, Alberto, et al., "Simultaneous Left Ventricular Echocardiography and Aortic Blood Velocity During Rapid Right Ventricular Pacing in Man," The American Journal of the Medical Sciences, Jan.-Feb. 1977 vol. 273, No. 1, pp. 55-62.

Watt, A.H., et al. "Intravenous Adenosine in the Treatment of Supraventricular Tachycardia; a Dose-Ranging Study and Interaction with Dipyridamole," British Journal of Clinical Pharmacology (1986), 21, 227-230.

Uchida, Barry T., et al., "Modifications of Gianturco Expandable Wire Stents," AJR:150, May 1988, Dec. 3, 1987, pp. 1185-1187.

Selby, M.D., J. Bayne, "Experience with New Retrieval Forceps for Foreign Body Removal in the Vascular, Urinary, and Biliary Systems," Radiology 1990; 176:535-538.

Inoune, M.D., Kanji, et al., "Clinical Application of Transvenous Mitral Commissurotomy by a New Balloon Catheter," The Journal of Thoracic and Cardiovascular Surgery 87:394-402, 1984.

Al Zaibag, Muayed, et al., "Percutaneous Balloon Valvotomy in Tricuspid Stenosis," British Heart Journal, Jan. 1987, vol. 57, No. 1, pp. 51-53.

Lawrence, Jr., M.D., David D., "Percutaneous Endovascular Graft: Experimental Evaluation," Radiology 1897; 163: 357-360.

Dotter, M.D., Charles T., "Transluminal Treatment of Arteriosclerotic Obstruction," University of Oregon's Minthorn Memorial Laboratory for Cardiovascular Research through Radiology, Circulation, vol. XXX, Nov. 1964, pp. 654-670.

Sigwart, Ulrich, "An Overview of Intravascular Stents: Old and New," Chapter 48, Textbook of Interventional Cardiology, $2^{nd}$ Edition, W.B. Saunders Company, Philadelphia, PA, © 1994, 1990, pp. 803-815.

Pavcnik, M.D., Ph.D., Dusan, et al. "Development and Initial Experimental Evaluation of a Prosthetic Aortic Valve for Transcatheter Placement," Cardiovascular Radiology 1992; 183:151-154.

Rashkind, M.D., William J., "Historical Aspects of Interventional Cardiology: Past, Present, Future," Texas Heart Institute Journal, Interventional Cardiology, pp. 363-367, 1986.

Rösch, M.D., Josef, "The Birth, Early Years and Future of Interventional Radiology," J Vasc Interv Radiol 2003; 14:841-853.

Ross, F.R.C.S., D.N., "Aortic Valve Surgery," Guy's Hospital, London, pp. 192-197, approximately 1968.

Rashkind, M.D., William J., "Creationof an Atrial Septal Defect Withoput Thoracotomy," the Journal of the American Medical Association, vol. 196, No. 11, Jun. 13, 1966, pp. 173-174.

Porstmann, W., et al., "Der Verschluβ des Ductus Arteriosus Persistens ohne Thorakotomie," Thoraxchirurgie Vaskuläre Chirurgie, Band 15, Heft 2, Stuttgart, im Apr. 1967, pp. 199-203.

* cited by examiner

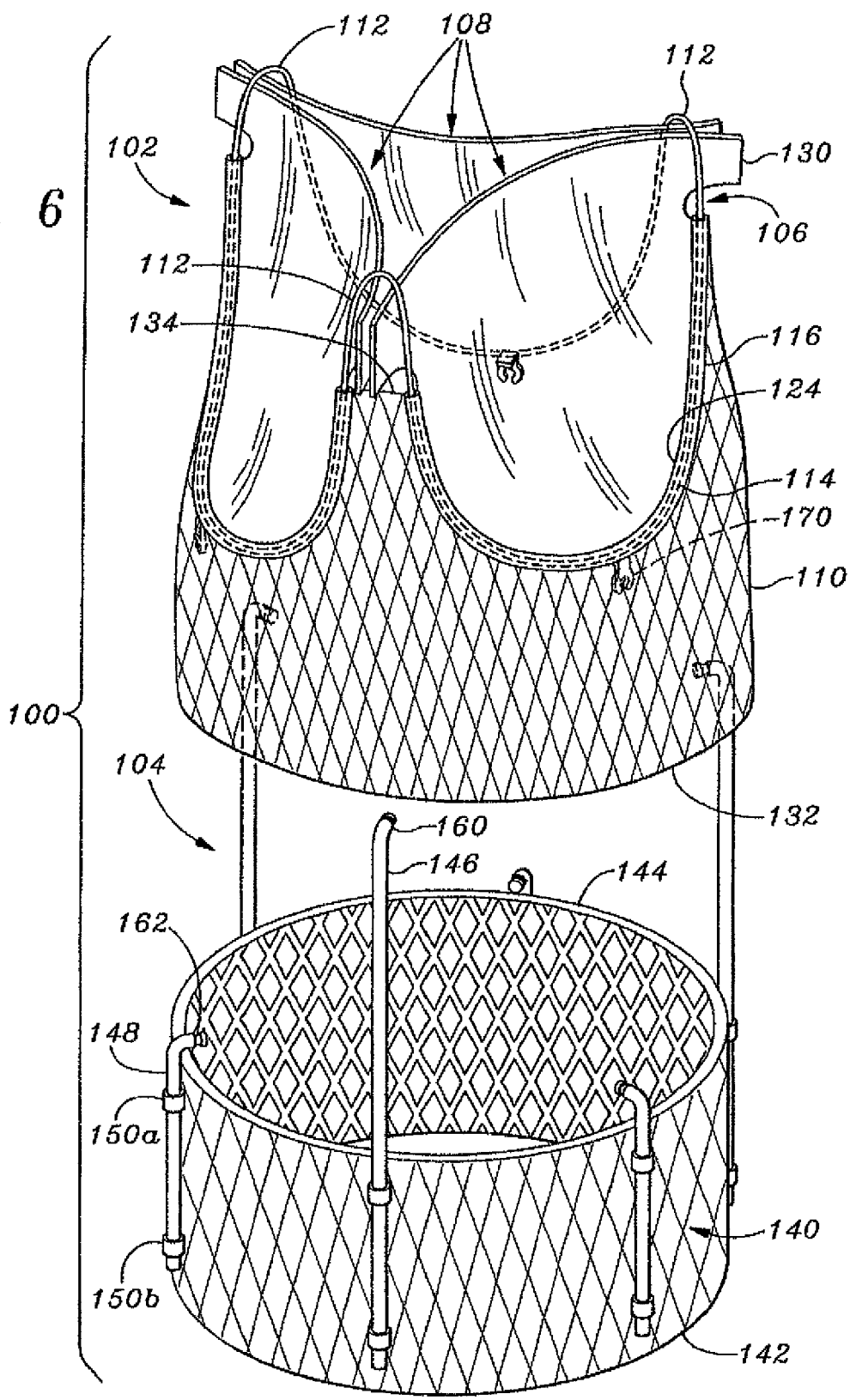

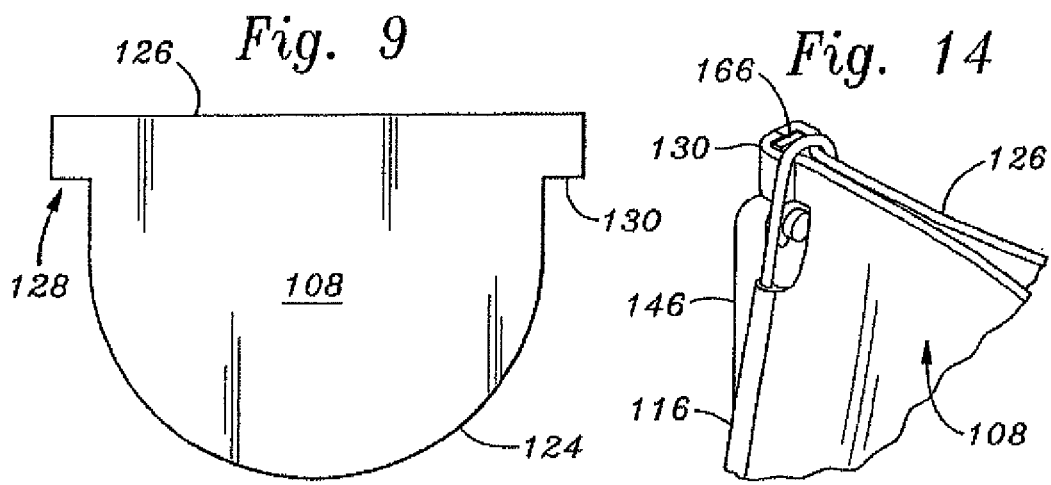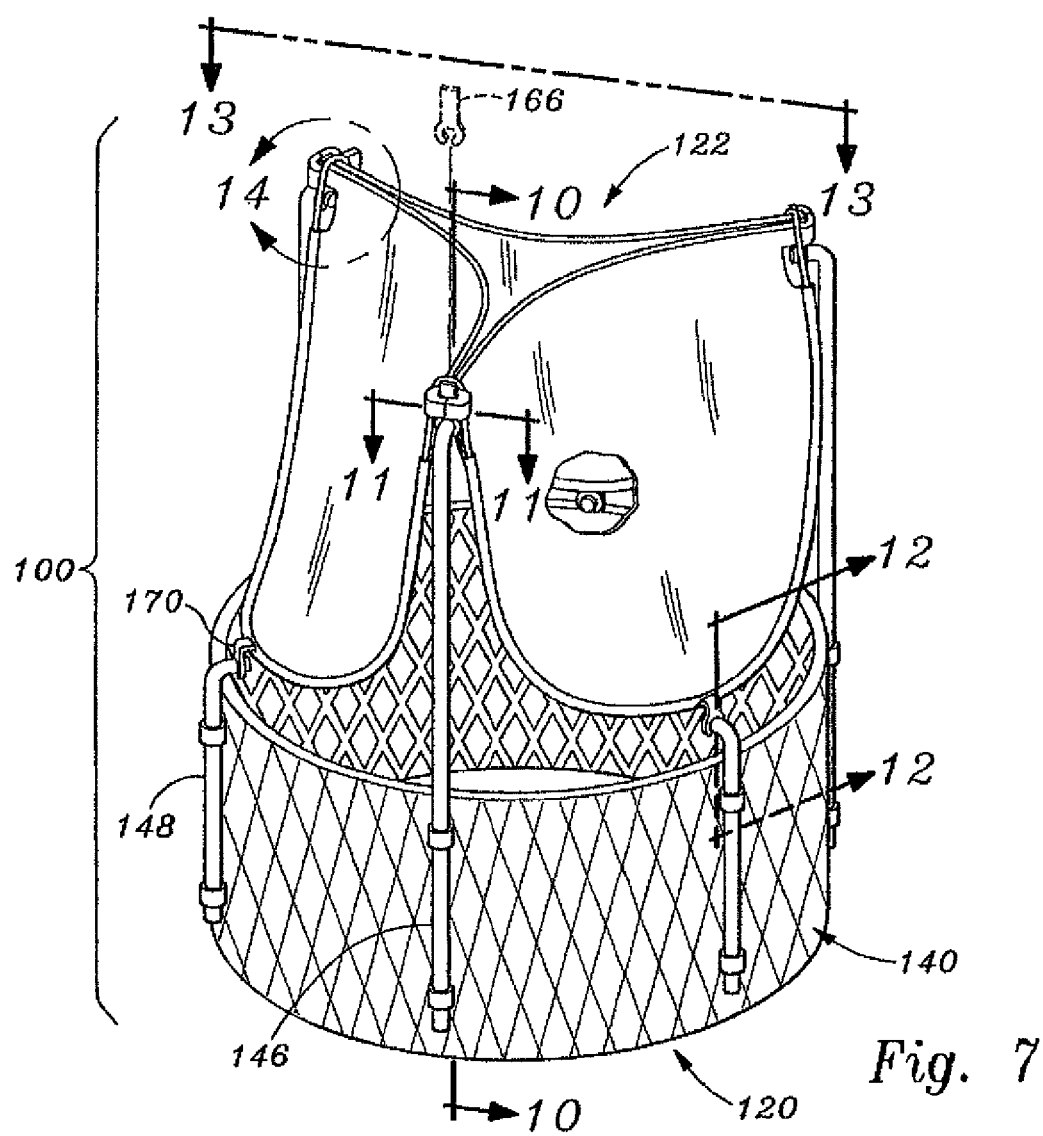

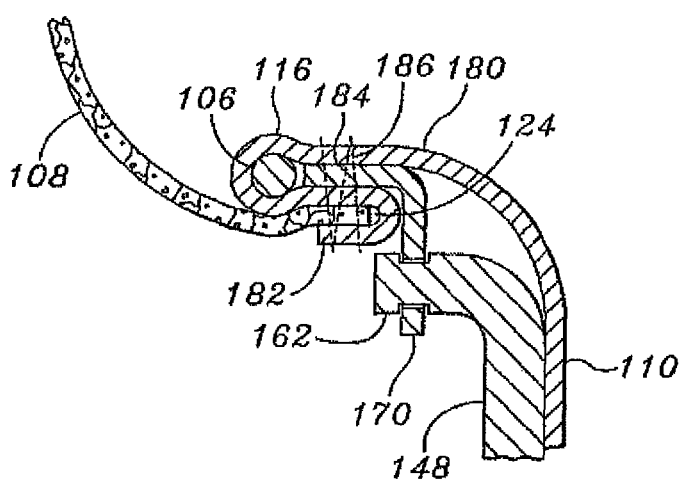
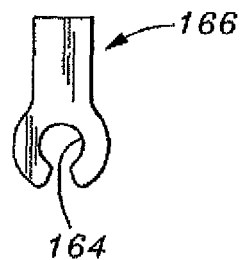
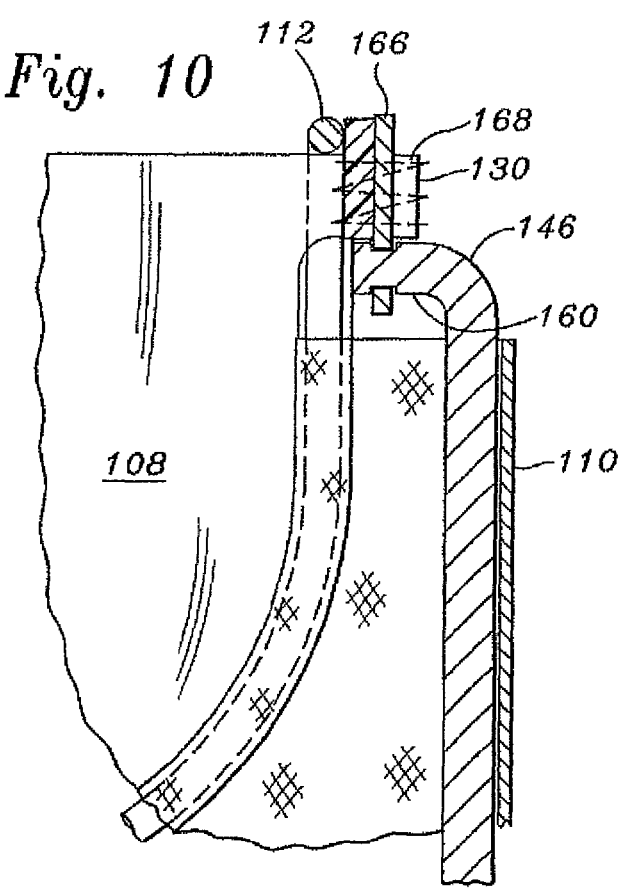
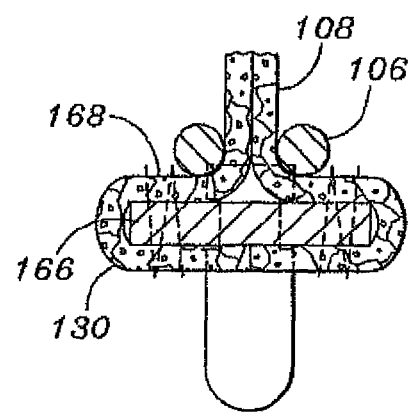

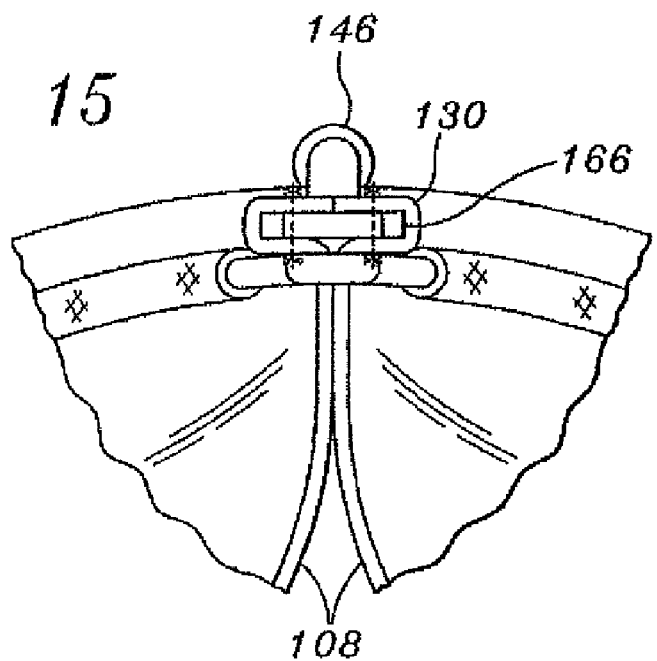
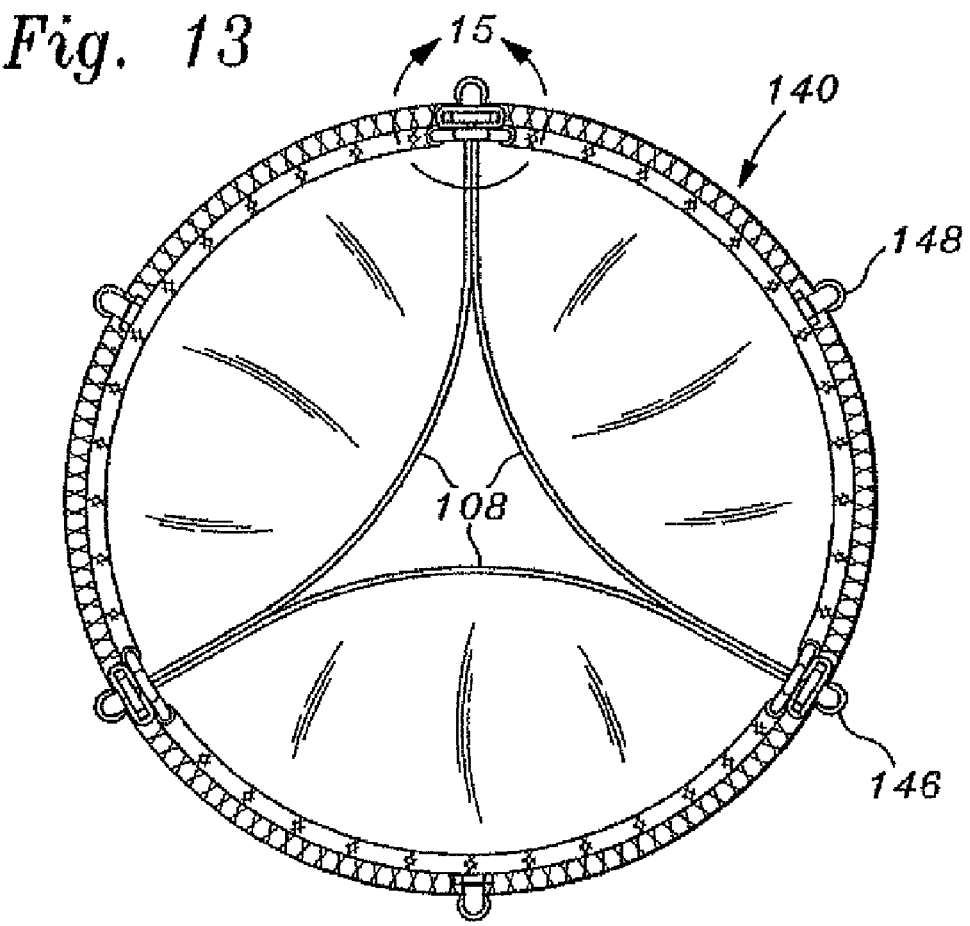

MINIMALLY-INVASIVE HEART VALVES

RELATED APPLICATIONS

The present application is a continuation of U.S. application Ser. No. 12/099,566, filed Apr. 8, 2008, now issued as U.S. Pat. No. 8,092,518, which is a continuation of U.S. application Ser. No. 10/766,139, filed Jan. 28, 2004, now issued as U.S. Pat. No. 7,381,218, which is a continuation of U.S. application Ser. No. 10/185,812, filed Jun. 28, 2002, now issued as U.S. Pat. No. 6,767,362, which is a divisional of U.S. application Ser. No. 09/549,413, filed Apr. 6, 2000, and now issued as U.S. Pat. No. 6,454,799.

FIELD OF THE INVENTION

The present invention relates generally to medical devices and particularly to expandable heart valve prostheses especially for use in minimally-invasive surgeries.

BACKGROUND OF THE INVENTION

Prosthetic heart valves are used to replace damaged or diseased heart valves. In vertebrate animals, the heart is a hollow muscular organ having four pumping chambers: the left and right atria and the left and right ventricles, each provided with its own one-way valve. The natural heart valves are identified as the aortic, mitral (or bicuspid), tricuspid and pulmonary valves. Prosthetic heart valves can be used to replace any of these naturally occurring valves, although repair or replacement of the aortic or mitral valves is most common because they reside in the left side of the heart where pressures are the greatest.

Where replacement of a heart valve is indicated, the dysfunctional valve is typically cut out and replaced with either a mechanical valve, or a tissue valve. Tissue valves are often preferred over mechanical valves because they typically do not require long-term treatment with anticoagulants. The most common tissue valves are constructed with whole porcine (pig) valves, or with separate leaflets cut from bovine (cow) pericardium. Although so-called stentless valves, comprising a section of porcine aorta along with the valve, are available, the most widely used valves include some form of stent or synthetic leaflet support. Typically, a wireform having alternating arcuate cusps and upstanding commissures supports the leaflets within the valve, in combination with an annular stent and a sewing ring. The alternating cusps and commissures mimic the natural contour of leaflet attachment. Importantly, the wireform provides continuous support for each leaflet along the cusp region so as to better simulate the natural support structure.

A conventional heart valve replacement surgery involves accessing the heart in the patient's thoracic cavity through a longitudinal incision in the chest. For example, a median sternotomy requires cutting through the sternum and forcing the two opposing halves of the rib cage to be spread apart, allowing access to the thoracic cavity and heart within. The patient is then placed on cardiopulmonary bypass which involves stopping the heart to permit access to the internal chambers. Such open heart surgery is particularly invasive and involves a lengthy and difficult recovery period.

Recently, a great amount of research has been done to reduce the trauma and risk associated with conventional open heart valve replacement surgery. In particular, the field of minimally invasive surgery (MIS) has exploded since the early to mid-1990s, with devices now being available to enable valve replacements without opening the chest cavity. MIS heart valve replacement surgery still requires bypass, but the excision of the native valve and implantation of the prosthetic valve are accomplished via elongated tubes or cannulas, with the help of endoscopes and other such visualization techniques.

Some examples of MIS heart valves are shown in U.S. Pat. No. 5,980,570 to Simpson, U.S. Pat. No. 5,984,959 to Robertson, et al., and PCT Publication No. WO 99/334142 to Vesely. Although these and other such devices provide various ways for collapsing, delivering, and then expanding a "heart valve" per se, none of them disclose an optimum structure for tissue valves. For instance, the publication to Vesely shows a tissue leaflet structure of the prior art in FIG. 1, and an expandable inner frame of the invention having stent posts in FIGS. 3A-3C. The leaflets are "mounted to the stent posts 22 in a manner similar to that shown in FIG. 1." Such a general disclosure stops short of explaining how to construct an optimum valve. In particular, the means of attaching the leaflets to the MIS stent is critical to ensure the integrity and durability of the valve once implanted. All of the prior art MIS valves fall short in this regard.

In view of the foregoing, it is evident that an improved sewing ring that addresses the apparent deficiencies in existing expandable heart valves is necessary and desired.

SUMMARY OF THE INVENTION

The present invention provides an expandable prosthetic heart valve for placement in a host heart valve annulus, comprising an expandable stent system adapted to be delivered in a collapsed state to an implantation site and expanded, and a plurality of prosthetic leaflets attached to the stent system. Each leaflet has an approximately semi-circular cusp edge terminating at each end in commissure portions, and a coapting edge extending between the commissure portions. Each leaflet is attached to the stent system substantially entirely along the cusp edge and at both commissure portions, with a coapting edge remaining unattached. The stent system may comprise an expandable generally annular tissue-engaging base and an elastic generally annular wireform attached thereto. The base is adapted to be delivered in a radially collapsed state and expanded into contact with the host annulus. The annular wireform defines a plurality of upstanding commissures and a plurality of arcuate cusps between adjacent commissures, and the prosthetic leaflets are attached to the wireform along the cusps and commissures, wherein the wireform and leaflets are configured to be radially compressed.

In one embodiment, the heart valve includes a plurality of upstanding posts attached to one of the tissue-engaging base and elastic wireform, each post having a connector. A plurality of mating connectors are provided on the other of the tissue-engaging base and elastic wireform for mating with the post connectors. The posts and mating connectors may be provided for each commissure and each cusp of the elastic wireform so that the valve includes a number of posts and mating connectors equal to the number of commissures plus the number of cusps. Further, the expandable stent system may include an undulating wireform defining a plurality of commissures and a plurality of cusps between adjacent commissures. The cusp edge of each of the prosthetic leaflets attaches along a wireform cusp, and the commissure portions of each leaflet terminate in outwardly extending tabs that each attach to a wireform commissure, wherein tabs from adjacent leaflets are attached together at each of the wireform commissures.

In another aspect of the invention, an expandable prosthetic heart valve for placement in a host heart valve annulus is provided. The heart valve comprises an expandable stent portion and an elastic leaflet portion connectable to the stent portion. The stent portion defines an inflow end of the valve and is adapted to be delivered in a collapsed state and expanded into contact with the host annulus. The leaflet portion forms a one-way flow occluder on an outflow end of the valve and includes an elastic wireform defining alternating cusps and commissures and prosthetic tissue attached substantially entirely therealong. The stent portion desirably includes a tubular member and a plurality of connectors, and wherein a plurality of connectors are provided on the elastic wireform for mating with the tubular member connectors. The wireform connectors may be provided on each commissure and on each cusp of the wireform so that the valve includes a number of mating connectors equal to the number of commissures plus the number of cusps. In a preferred embodiment, the prosthetic tissue comprises a plurality of individual leaflets secured along the alternating cusps and commissures of the elastic wireform. Additionally, the wireform may have a fabric covering, wherein the individual leaflets are stitched along the fabric covering. The fabric covering continues toward an inflow end of the valve in a skirt that surrounds the stent portion and is adapted to be captured between the expanded stent portion and the host annulus. A plurality of posts rigidly may connect to the stent portion and extend upward within the skirt into mating connection with the elastic wireform.

In a still further aspect, the present invention provides a two-part expandable prosthetic heart valve for placement in a host heart valve annulus, comprising:
  a leaflet subassembly having a wireform defining a plurality of upstanding commissures and a plurality of arcuate cusps extending between adjacent commissures, a midpoint of each cusp being located approximately equidistant from the adjacent commissures;
  a generally annular tissue-engaging base defining an axis; and
  a system for connecting the leaflet subassembly and the tissue-engaging base, including a plurality of mating connectors on the leaflet subassembly and on the tissue-engaging base, wherein one connector each is provided at each commissure, and one at each cusp midpoint.

In the two-part heart valve, the tissue-engaging base preferably comprises an expandable tubular member that is deliverable to the host annulus in a collapsed state and expandable into contact with the host annulus to secure the valve therein. Furthermore, the tissue-engaging base forms an inflow end of the valve, and the system for connecting the leaflet subassembly and tissue-engaging base includes a plurality of posts coupled to the tubular member and having varying lengths extending away from the inflow end of the valve. A first plurality of posts each having a first length connects with the wireform commissures, and a second plurality of posts each having a second length connects with the wireform cusps shorter than the first length. The mating connectors may be configured to be joined together by axial compression, preferably with a snap-fit configuration.

A further aspect of the invention includes a prosthetic heart valve having a support stent and a flexible tubular member. The support stent includes a tubular base along an inflow end a plurality of generally axially-extending commissure posts disposed evenly around the tubular base on an outflow end thereof. The flexible tubular member has a prosthetic section attached to the commissure posts so as to define a plurality of the prosthetic valve leaflets between the posts, and a fabric section connected to the base. The prosthetic section and fabric section are desirably both generally tubular and attached together at a seam, wherein the seam is spaced from the outflow end of the tubular base so that only the fabric section of the flexible tubular member contacts the tubular base. The commissure posts each may have an axial slot, wherein the tubular member is primarily located within the posts except for a plurality of loops that extend outward through each slot on each post. A plurality of inserts sized larger than the slots may be provided, each of which insert is captured within a loop extending outward through each slot to retain the loop through the slot. In a preferred embodiment, the commissure posts are integrally formed with the base, the base and commissure posts being initially formed from a flat section of material, wherein the commissure posts initially extend from the inflow end of the base and are bent 180° to extend alongside the base and project beyond the base at the outflow end thereof.

A prosthetic heart valve of the present invention has a support stent including a tubular base along an inflow end. A plurality of generally axially-extending commissure posts each having an axial slot is disposed evenly around the tubular base on an outflow end thereof. A flexible tubular member having an outflow edge is primarily located within the posts except for a plurality of loops that extend outward through each slot on each post. Further, a plurality of inserts sized larger than the slots are provided, each of which insert is captured within a loop extending outward through each slot to retain the loop through the slot, the outflow edge of the tubular member defining a plurality of valve leaflets. The tubular base may be plastically-expandable from a first size adapted for minimally invasive delivery, to a second, functional size that fits within a heart valve annulus.

A method of minimally-invasive heart valve replacement surgery on a patient is also provided by the present invention. The method includes the steps of:
  providing an annular tissue-engaging base, the base being expandable from a collapsed state;
  providing a generally annular elastic wireform subassembly having a plurality of prosthetic leaflets connected thereto, the elastic wireform subassembly having a relaxed, expanded size and a compressed, reduced size;
  connecting the wireform and leaflets to the base to form a heart valve;
  delivering the heart valve with the connected base in its collapsed state and wireform subassembly in its reduced size to an annulus of the patient's heart valve being replaced; and
  expanding the base into its expanded state in contact with the annulus.

The step of delivering the heart valve to the annulus may be accomplished by passing the valve through the patient's vasculature or via a minimally-invasive port in the patient's chest. The tissue-engaging base may plastically-expandable from its collapsed state to its expanded state, and the step of expanding the plastically-expandable base comprises inflating a balloon within the annular base.

A further understanding of the nature and advantages of the invention will become apparent by reference to the remaining portions of the specification and drawings.

BRIEF DESCRIPTION OF THE DRAWINGS

FIG. 6 is an exploded perspective view of a second embodiment of an expandable heart valve of present invention having two detachable components designed to be assembled post-storage, including a tissue-engaging base and a wireform-supported leaflet subassembly;

FIG. 7 is an assembled perspective view of the expandable heart valve of FIG. 6, with a fabric skirt removed to illustrate details of a connecting system between the base and leaflet subassembly;

FIG. 8 is a plan view of an insert used to both attach individual leaflets to commissures of the wireform, and connect the commissures of the leaflet subassembly to the tissue-engaging base of the expandable heart valve of FIG. 6;

FIG. 9 is a plan view of an individual leaflet for use in the expandable heart valve of FIG. 6;

FIG. 10 is a longitudinal cross-sectional view taken along line 10-10 of FIG. 7;

FIG. 11 is a transverse cross-sectional view taken along line 11-11 of FIG. 7;

FIG. 12 is a longitudinal cross-sectional view taken along line 12-12 of FIG. 7;

FIG. 13 is a top plan view of the expandable heart valve taken along line 13-13 of FIG. 7;

FIG. 14 is an enlarged perspective view of a commissure region of the expandable heart valve taken within the circle 14 of FIG. 7;

FIG. 15 is an enlarged plan view of the commissure region of the expandable heart valve taken within the circle 15 of FIG. 13.

DESCRIPTION OF THE PREFERRED EMBODIMENTS

The present invention discloses two different expandable heart valves for implantation in a host annulus, or host tissue adjacent the annulus. The valves may be implanted in any of the four valve positions within the heart, but are more likely to be used in replacing the aortic valve because of the circular shape of the annulus.

It should also be noted that the specific constructional details, including materials and shapes, may be varied from those shown. For example, an expandable tubular base is used in both valve embodiments, and is described as being a plastically-expandable structure that radially expands into contact with the annulus tissue. Alternatively, the tubular base may be elastically- or self-expandable, or expandable on the application of heat (i.e., using shape memory material). Further, various means are known for plastically or elastically expanding structures into contact with anatomical passageways, and though the present invention illustrates and describes only one such structure, others may be used to practice the invention. For example, any plastically- or elastically-expandable structure may be modified so as to have a suitable diameter for heart valves and used to practice the present invention. In addition, barbs, flanges, staples, and the like may be added to the tubular base for the purpose of greater attachment to the host tissue. In short, the present invention should not be construed to be limited to the particular structures and materials disclosed, the scope of the invention being solely defined by the appended claims.

With reference to FIGS. 1-5, a first embodiment of an expandable prosthetic heart valve 20 is shown and described. The prosthetic heart valve 20 is assembled prior to storage. In a second embodiment, shown in FIGS. 6-15, a second embodiment of an expandable heart valve is shown and described. Detachable components of the expandable heart valve in the second embodiment are separately stored, and assembled just prior to insertion and delivery to the host annulus, which provides certain advantages to be described.

Pre-Assembled Expandable Heart Valve

Figure 1:
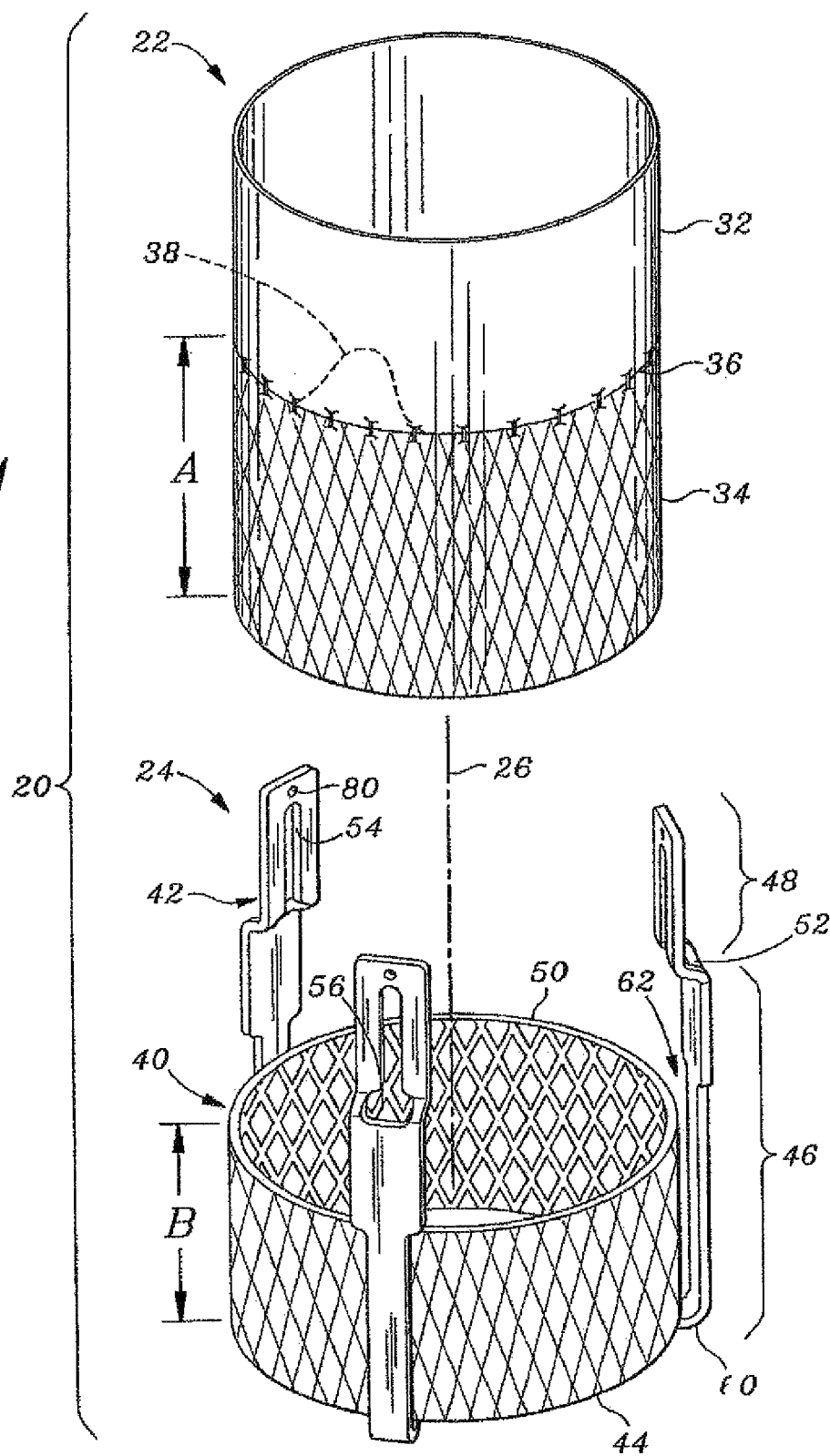
FIG. 1 is an exploded perspective view of a first embodiment of an expandable heart valve of the present invention, including a support stent and a flexible tubular member.
Figure 2:
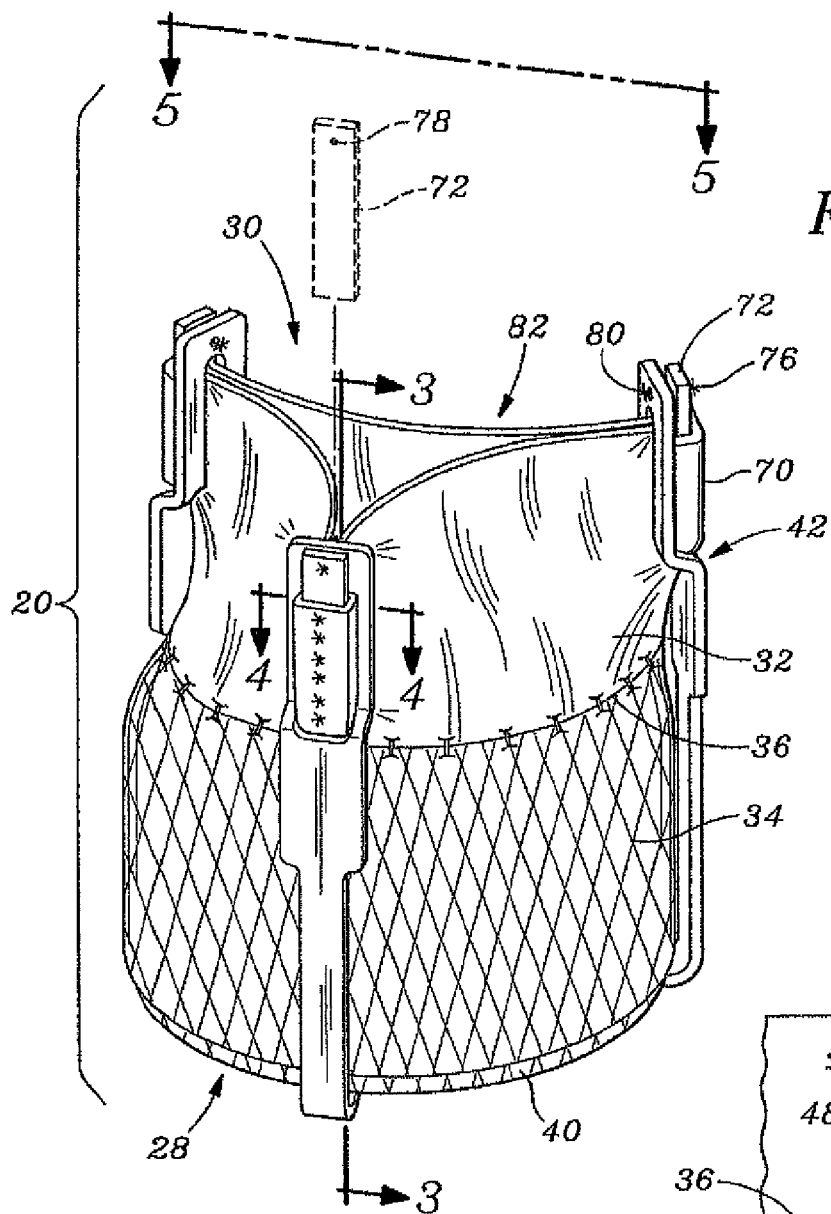
FIG. 2 is an assembled perspective view of the expandable heart valve of FIG. 1.

FIG. 1 illustrates the first embodiment of the expandable heart valve 20 exploded, with a flexible tubular member 22 separated from a support stent 24 along a central axis 26. FIG. 2 illustrates the flexible tubular member 22 attached to the support stent 24 to form the assembled heart valve 20. The heart valve 20 has an inflow end 28 (the lower end in the figure) and an outflow end 30 (the upper end in the figure).

The flexible tubular member 22 comprises a leaflet section 32 connected to a fabric section 34 at a seam 36. As illustrated, both the leaflet section 32 and fabric section 34 are desirably formed as tubes, such that the seam 36 defines a circle therebetween. Alternatively, the seam 36 may be other than circular if areas of the leaflet section 32 or fabric section 34 need to be expanded around their circumferential juncture. For example, the fabric section 34 may need to be increased in the commissure region of the valve 20, such as indicated by the dashed line 38 in FIG. 1. Whatever the configuration, the fabric section 34 has a minimum axial height indicated at A.

Desirably, the leaflet section 32 is formed from pericardial tissue, such as bovine or equine pericardium, suitably treated to render it biocompatible. Of course, any suitable leaflet material, including synthetics, may be used. The fabric section 34 is desirably a woven polyester, such as polyethylene terepthalate. Alternatively, the fabric section 34 may be formed of polytetrafluoroethylene (PTFE), or other suitable biocompatible sheet material. Still further, the leaflet section 34 may extend the entire axial height of the flexible tubular member 22, with the fabric section 34 being wrapped around and attached to the inflow end.

As seen in FIG. 1, the support stent 24 comprises a tubular base 40 and a plurality of upstanding commissure posts 42 distributed evenly around the periphery thereof. That is, the tubular base 40 is provided at the inflow end 28 of the support stent 24, with the commissure posts 42 extending in the outflow direction. Desirably, there are three such commissure posts 42 disposed at 120° intervals about the circumference of the stent 24. The tubular base 40 has an axial height indicated at B, which height is less than the axial height A of the fabric section 34 of the flexible tubular member 22. The commissure posts 42 extending upward a sufficient distance such that the entire axial dimension of the support stent 24 is slightly greater than the axial dimension of the flexible tubular member 22, as indicated in the assembled view of FIG. 2.

The tubular base 40 comprises a plastically-expandable material that can be expanded into the configuration shown in the figures from a radially compressed configuration (not shown). In this regard, the illustrated tubular base 40 essentially comprises a non-self expanding stent that can be expanded from its compressed state using a balloon inflated from within the base, for example. Numerous configurations of such plastically-expandable tubes are available in the prior art, and as mentioned above, the present invention should not be considered limited to any one configuration. Moreover, in other configurations the base 40 may be self- or heat-expandable.

With reference to FIG. 1, each commissure post 42 attaches to or extends from an inflow rim 44 of the tubular base 40, continuing on the outside of the tubular base toward the outflow end in an elongated axially-extending lower section 46, and terminating in an axially extending upper section 48. The upper section 48 commences at a predetermined distance above an outflow rim 50 of the tubular base 40 and is stepped radially inward from the lower section 46 at a transition region 52. An axial slot 54 is provided in the upper section 48 and in the transition region 52. The width of the axial slot 54 is desirably constant in the upper section 48, but increases at a relief region 56 in the transition region 52.

In a preferred embodiment, the commissure posts 42 are formed of a biocompatible, elastic material, preferably metallic. For example, each commissure post 42 may be formed of stainless-steel, titanium, or Elgiloy. Alternatively, the commissure posts 42 may be a biocompatible polymer, such as Delrin or polyacetyl.

In a preferred embodiment, the support stent 24 is formed from a single piece of flat material. Specifically, the tubular base 40 initially comprises a flat, narrow strip of uniform width material with the commissure posts 42 extending from one long side thereof. Using conventional means, the narrow strip of material is then rolled into the tubular shape shown in the figures, and the juxtaposed narrow ends joined by, for example, crimping. Each of the commissure posts 42 is then bent 180° outward to project in the opposite direction from their original direction. FIG. 1 illustrates such a configuration in which a 180° bend 60 joins each commissure post 42 to the inflow rim 44. The radius of the bend 60 is such that a narrow space 62 is defined between the lower section 46 of each commissure post 42 and the exterior of the tubular base 40.

The flexible tubular member 22 attaches to the support stent 24 as seen in FIG. 2, with the leaflet section 32 connected to the commissure posts 42, and the fabric section 34 connected to the tubular base 40. More specifically, the fabric section 34 surrounds the tubular base 40 and extends toward the inflow rim 44 in the spaces 62 created inboard of each commissure post 42. Although not shown, the fabric section 34 may be attached to the exterior of the tubular base 40, such as by sutures passed through the fabric and through openings in the tubular base. Because the axial dimension A of the fabric section 34 is greater than the axial dimension B of the tubular base 40, the seam 36 is disposed above the outflow rim 50 (FIG. 1) of the base. This is more clearly shown in the cross-section of FIG. 3.

Figure 3:
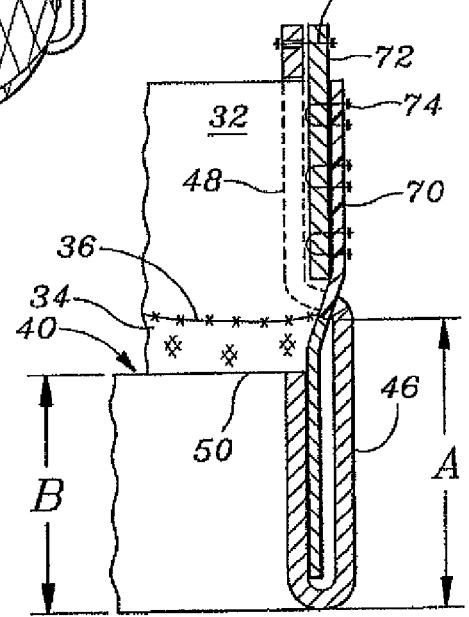
FIG. 3 is a longitudinal cross-sectional view taken along line 3-3 through a commissure of the expandable heart valve of FIG. 2.

The leaflet section 32 is disposed substantially between the commissure posts 42, except for a number of loops 70 threaded outward through the axial slots 54. As seen FIGS. 2-3, the loops 70 comprises regions of the tubular leaflet section 32 pinched and threaded through the axial slots 54. A plurality of inserts 72 are used to secure the loops 70 to the exterior of the commissure posts 42. That is, as seen FIG. 4, the inserts 72 each have a width W that is greater than the circumferential width of the axial slots 54. Because the inserts 72 are disposed within the loops 70, they prevent the loops from pulling inward again through the axial slot 54. A plurality of stitches 74 are preferably provided to secure the leaflet section 32 to the inserts 72. In addition, as seen in FIG. 3, stitching 76 passes through an aperture 78 in each insert 72, and through an aperture 80 provided in the outflow end of each commissure post 42. In this manner, each insert 72 is secured with respect to the support stent 24.

Figure 5:
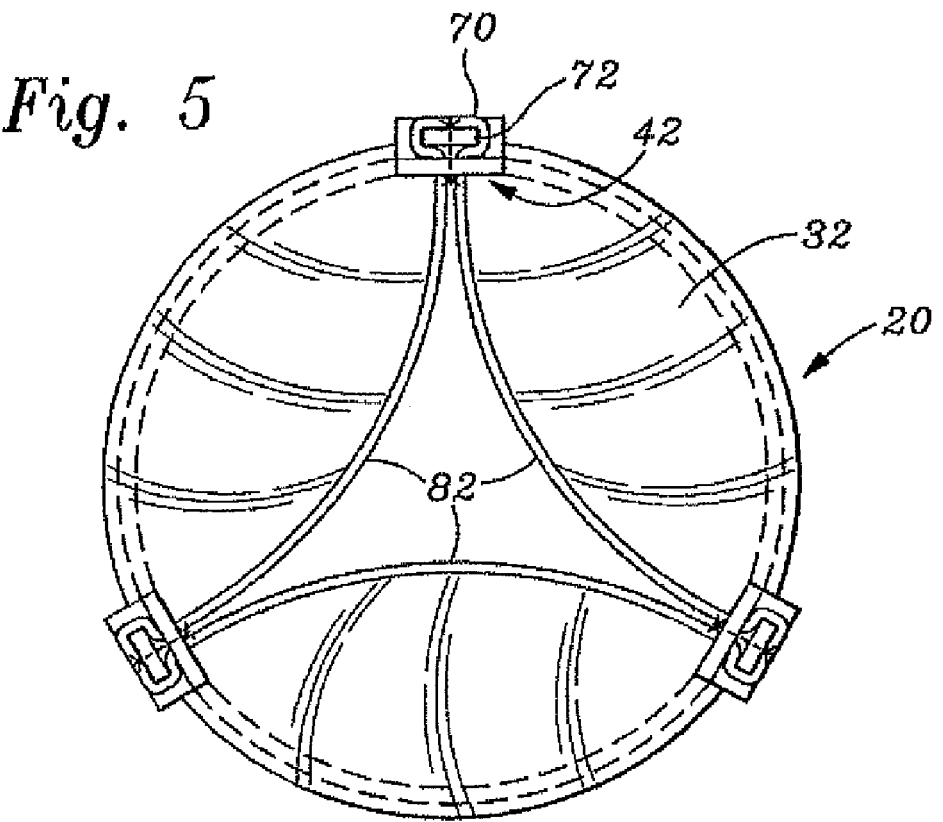
FIG. 5 is a top plan view of the expandable heart valve of FIG. 2.

With reference to FIGS. 2 and 5, a plurality of leaflets 82 are defined between the support stents 24 by the leaflet section 32. Specifically, where there are three stent post 24, a generally triangular arrangement of leaflets 82 remains unconstrained in the middle portion of the valve 20 and opens and closes depending on blood flow forces. Furthermore, the continuous flexible tubular member 22 provides a flow channel for blood through the valve 20. When the pressure differential is such that blood flows into the inflow end 28 of the valve 20, the leaflets 82 spread apart and the valve opens. Conversely, when the pressure differential reverses, the leaflets 82 come together, or coapt, to close the valve 20.

Figure 4:
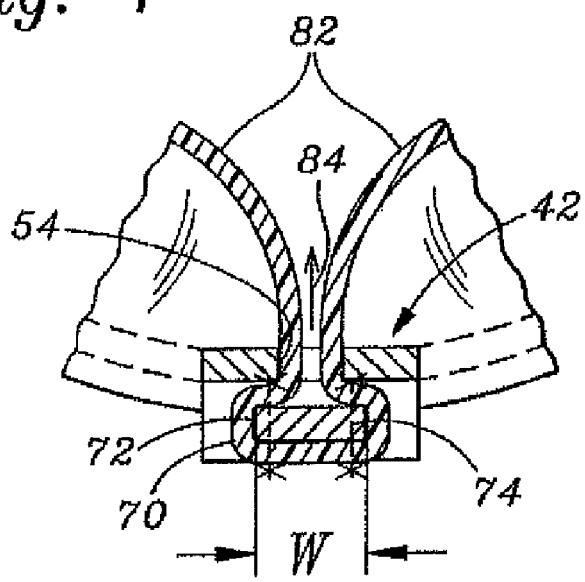
FIG. 4 is a transverse cross-sectional view taken along line 4-4 through the commissure of the expandable heart valve of FIG. 2.

When the pressures are such that the valve closes, radially inward forces are imposed on the free edge of the leaflet section 32, which may tend to cantilever the support stents 24 inward a slight amount. Localized stresses on the leaflet section 32 are reduced at the connection with the stent supports 24, however, because of the use of the inserts 72 within the loops 70. That is, as best seen in FIG. 4, radially inward forces on the leaflets 82 as indicated by the arrow 84, pull the inserts 72 inward such that the leaflet material is clamped between each insert and the respective commissure post 42. Although stitching 74 through the leaflet section 32 is provided, such stitching is not subjected to direct tensile stresses, and thus is less likely to tear through the leaflet tissue.

Certain features of the valve 20 reduce wear typically associated with stent-leaflet dynamic contact. First, because the axial dimension A of the fabric section 34 is greater than the dimension B of the tubular base 40, any contact between the flexible tubular member 22 and the tubular base 40 (at the outflow rim 50) is between fabric and the base. That is, the leaflet section 32 is not placed in contact with the base 40, thus increasing the life of the valve. Additionally, the enlarged relief region 56 of the slot 54 in the transition region 52 helps reduce the rubbing that might otherwise occur between the commissure posts 42 and the leaflets 80. That is, the leaflet section 32 continues substantially axially downward from the loops 70, as seen in FIG. 3, and the relief region 56 provides a small gap in the transition region 52 between the leaflet tissue and the sides of the slot 54 to help prevent rubbing therebetween.

In use, the assembled heart valve 20 as seen in FIG. 2 is initially provided in a radially compacted configuration (not shown). Preferably, the valve 20 is loaded about a balloon catheter and within a delivery cannula. The balloon catheter with the valve 20 loaded thereon is then passed through the patient's vasculature (or through an access port in the chest) into proximity with the host annulus. Alternatively, where the chest of the patient is opened, the reduced size valve 20 is inserted into position using a holder.

Once in position within the annulus of the valve being replaced, the balloon (or other expanding means) causes the tubular base 40 to expand into contact with the annulus. Actually, because the commissure posts 42 and fabric section 34 surround tubular base 40, these elements are compressed against the host annulus. Because the tubular base 40 is plastically-expandable, it substantially retains its expanded shape. A slight over-expansion of the tubular base 40 may be required to compensate for any elastic spring-back character of the material used. Again, barbs or staples may also be utilized to further secure the valve 20 and in place. Ultimately, the balloon catheter is deflated and removed from within the valve 20.

Expandable Heart Valve Assembled Post-Storage

FIGS. 6-15 illustrate an expandable prosthetic heart valve 100 including, as best seen in FIG. 6, a leaflet subassembly 102 adapted to connect to a tissue-engaging base 104. The two components are both shown in FIG. 6 in their radially expanded configurations, though both are designed to be radially compressed and delivered through a catheter or cannula, for example. In contrast with the first embodiment, however, the two components are stored separately, and connected just prior to delivery into the body of the patient. In general, the two components provide a tissue-engagement ring and a relatively more flexible valve member having fluid occluding surfaces. It should be understood that configurations of these two connectable components other than those specifically shown may be encompassed by the appended claims.

As seen in FIG. 6, the leaflet subassembly 102 comprises an elastic wireform 106 supporting a plurality of prosthetic leaflets 108, and a fabric skirt 110. The wireform 106 comprises a continuous undulating pattern of alternating commissures 112 and cusps 114. Preferably, the valve 100 is a trileaflet type, such that the wireform 106 has three commissures 112 and three cusps 114, with three leaflets 108 support thereby. In particular, each leaflet 108 is desirably attached to adjacent commissures 112, and along the entire arcuate cusp 114 therebetween. As will be described in more detail below, the leaflets 108 each attach to a fabric covering 116 around the wireform cusps 114. In a preferred embodiment, the elastic wireform 106 is formed of a biocompatible, elastic material, preferably metallic. For example, the elastic wireform 106 may be formed of stainless-steel, titanium, or Elgiloy. Alternatively, the elastic wireform 106 may be formed from a biocompatible polymer, such as Delrin or polyacetyl. In this sense, therefore, the term "wire" in wireform should not be construed as limiting the material to metallic.

FIG. 7 illustrates an assembled valve 100 with the fabric skirt 110 shown in FIG. 6 removed for clarity. That is, the fabric skirt 110 is sized to drape outside of and surround the tissue-engaging base 104, but is removed in FIG. 7 to show the connection details between the base and the leaflet subassembly 102. The valve 100 defines an inflow end 120 and an outflow end 122.

FIG. 9 illustrates an exemplary leaflet 108 having an arcuate cusp edge 124 opposite a linear coapting edge 126. The cusp edge 124 is generally semi-circular, and terminates at commissure portions 128. A pair of oppositely-directed tabs 130 extend outward from both ends of the coapting edge 126, and are seen in FIG. 6 prior to attachment to the wireform 106. That is, the tabs 130 from adjacent leaflets 108 join together and pass through the inverted U-shaped commissures 112 of the elastic wireform 106. In a preferred embodiment, each leaflet 108 is formed from pericardial tissue, such as bovine or equine pericardium, or a synthetic material, that has been suitably treated to render it biocompatible.

With reference again to FIG. 6, the cusp edge 124 of each leaflet 108 is shaped so as to follow a cusp 114 of the elastic wireform 106. The fabric skirt 110 extends to an inflow edge 132 from each of the cusps 114, and when the skirt is assembled to the tissue-engaging base 104, the inflow edge extends substantially to the inflow end 120 (FIG. 7) of the valve. The fabric skirt 110 further terminates at outflow edges 134 between adjacent wires of the wireform commissures 112, below the leaflet tabs 130 extending therethrough. The skirt 110 may be made of a biocompatible fabric such as polyester, or of other suitable biocompatible sheet material.

The leaflet subassembly 102 attaches to the tissue-engaging base 104 at discrete locations, securely coupling each of the commissures 112 and cusps 114 of the elastic wireform 106 to the base. As seen best in FIG. 6, the tissue-engaging base 104 comprises a tubular plastically-expandable member 140 having an inflow rim 142 and outflow rim 144. A plurality of commissure posts 146 are either rigidly attached to, or securely coupled to, the tubular member 140 so as to extend generally axially beyond the outflow rim 144 in the outflow direction. Likewise, a plurality of cusp posts 148 are rigidly attached to, or securely coupled to, the tubular member 140 so as to extend beyond the outflow rim 144. Because the commissure posts 146 couple to the wireform commissures 112, they are longer than the cusp posts 148 that couple to the wireform cusps 114.

As illustrated, both the commissure posts 146 and cusp posts 148 extend through upper and lower sleeves 150a, 150b, respectively provided on the exterior of the tubular member 140, and are desirably axially secured therein. It should be noted that this is only one of numerous possible ways to rigidly couple upstanding posts to a plastically-expandable tubular member. However, the posts 146,148 are desirably located on the outside of the tubular member 140 so as not to interfere with a balloon for expanding the tubular member from the inside, nor to interfere with blood flowing through the valve. It should also be noted that in a reverse configuration, the posts 146, 148 may be initially attached to the wireform commissures 112 and cusps 114, respectively, as part of the leaflet subassembly 102 and subsequently connected to mating structures (not shown) provided on the tissue-engaging base 104.

A plurality of connectors are provided for attaching the elastic wireform 106 to the posts 146, 148 of the tissue-engaging base 104. In particular, as seen in FIG. 6, each commissure post 146 provides a lower commissure connector 160 thereon Likewise, each cusp posts 148 provides a lower cusp connector 162. In the illustrate embodiment, the outflow end of each of the posts 146, 148 is bent 90° to face radially inward, and a groove formed therein defines the respective connectors 160,162.

FIGS. 9-11 illustrate the configuration of the connection between the leaflet subassembly 102 and tissue-engaging base 104 at the commissures of the valve. With specific reference to FIG. 10, the lower commissure connector 160 of the commissure post 146 mates with an upper commissure connector 164 of an insert 166 (isolated in FIG. 8) secured to the wireform commissure 112. As seen in FIG. 11, adjacent leaflets 130 extend radially outward between spaced wires of the wireform 106 and wrap around the insert 166 to be connected on an outer side thereof with a plurality of stitches 168. FIG. 8 illustrates one form of the insert 166 wherein the upper commissure connector 164 comprises a downwardly opening partial circle which mates with the groove of the lower commissure connector 160, as seen in FIG. 10. In this manner, the commissures 112 are securely fastened with respect to the tissue-engaging base 104 by virtue of the interaction between the lower commissure connector 160 and upper commissure connector 164.

With reference again to FIGS. 6 and 7, a plurality of upper cusp connectors 170 attach to the approximate midpoint of each of the cusps 114 of the wireform 106. Each upper cusp connectors 170 is configured and positioned to mate with the lower cusp connector 162 formed on each of the cusp posts 140. Again, the upper cusp connector 170 may be provided with a downwardly opening partial circle that mates with the groove of the lower cusp connector 162.

With specific reference to FIG. 12, certain constructional details of the valve cusps are further illustrated. The fabric covering 116 of the wireform 106 is shown as a tube having an upper fabric extension 180 and a lower fabric extension 182 sandwiched around a radial portion 184 of the upper cusp connector 170. The upper cusp connector 170 extends outward and bends 90° downward to mate with the lower cusp connector 162. The upper fabric extension 180 continues outward and downward in the fabric skirt 110. The lower fabric extension 182 bends 180° underneath the cusp edge 124 of the respective leaflet 108. Stitching 186 secures the combined layers of the upper extension 180, radial portion 184, first part of the lower extension 182, leaflet cusp 124, and wrapped-around portion of the lower extension 182.

Desirably, both the insert 166 and upper cusp connector 170 are made from a suture-permeable material having sufficient strength to maintain the connections between the leaflet subassembly 102 and tissue-engaging base 104. For example, the insert 166 and connector 170 may be made of Delrin, or other suitable polymer. As illustrated, each of the connectors 164 and 170 are partial circles that fit around tubular grooves in the respective posts 146,148. Of course, other arrangements are possible, and the present invention should not be considered limited to those connectors illustrated.

As with the earlier embodiment, the valve 100 utilizes a low-stress connection between the leaflets 108 and the elastic wireform 106. In particular, as seen in FIG. 11, the provision of the insert 166 provides a clamping force during diastole between the insert and the wireform 106 against the portion of the leaflets 108 therebetween. The stitching 168 is not subjected to direct tensile stresses, and there is thus less chance for tearing.

Leaflet subassembly 102 is desirably stored in its expanded state, as seen in FIG. 6 (which, as mentioned, does not illustrate the commissure attachment structure). That is, the wireform 106 and leaflets 108 may be stored immersed in a preservative such as glutaraldehyde in a sterile container until needed. In this regard, the prosthetic leaflets 108 remain in their functional shape during storage. This greatly reduces adverse wrinkling or other permanent or semi-permanent damage to the leaflets over time, and improves the quality of the valve 100. At the same time, the base 104 desirably does not include any bioprosthetic or otherwise perishable components, and thus may be stored in a separate dry sterile container. This method also permits the combination of different bases with any one leaflet subassembly 102, or visa versa. For example, the type of attachment mechanism (i.e., staples, barbs, sutures, etc.) of the base 104 to the annulus may be selected by the surgeon, with different bases being attached in different ways, and all being combinable with a particular leaflet subassembly 102. Also, the type of base may be selected based on patient indications; with a self-expanding base being preferred in some situations and a balloon-expanded base in others.

In use, the leaflet subassembly 102 is compressed from its expanded configuration to a size corresponding to the tissue-engaging base 104 in its compressed state (not shown). If the tissue-engaging base 104 is plastically deformable then it is initially supplied in its compressed state. Alternatively, a self-expandable base 104 will have to be compressed either before or after connection to the similarly configured leaflet subassembly 102. Compression of the leaflet subassembly 102 (and base if necessary) may be accomplished using a tapered mandrel through which the subassembly is passed, or with a cinch or other direct constricting means. The two components are then connected together, just prior to insertion into the patient's body, and the valve 100 delivered simultaneously to the host annulus site. To connect the two components, the fabric skirt 110 is passed around the outside of the commissure posts 146 and around the tubular member 140. Each of the upper connectors 164 and 170 are caused to mate with the lower connectors 160, 162. In the illustrated embodiment, such a mating operation simply requires forcing each of the partial circles defining the upper connectors over the grooves defining the lower connectors. The partial circles open slightly, but then spring inward when the connectors snap together and the groove is fully seated.

There are a number of ways to deliver the valve 100 to the aortic annulus. For one, the tubular member 140 may be mounted around a balloon catheter and inserted via an introducer or other cannula into the patient's vasculature and to the aorta. Alternatively, an open-heart procedure or less-invasive port procedure may be utilized, with the tissue-engaging base 104 being delivered to the host annulus using a holder or other such means.

Figure 16A:
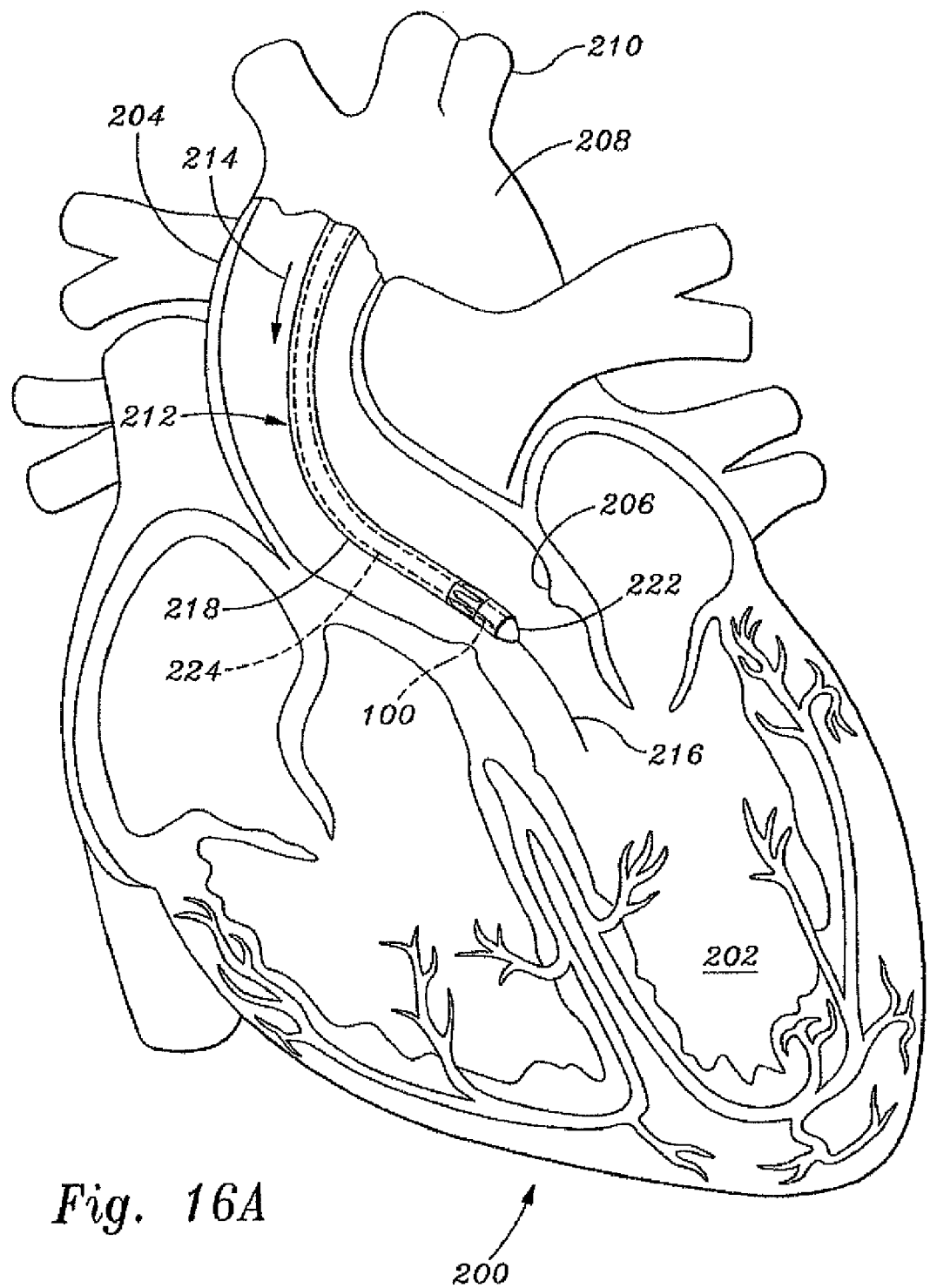
FIG. 16A-C illustrate a heart in section and several steps in a delivery and implantation procedure of the expandable valve of the present invention.

FIG. 16A depicts a sectional view of a heart 200 having a left ventricle chamber 202 opening to an ascending aorta 204 through an aortic annulus 206. The ascending aorta 204 continues over an aortic arch 208, and branches off into several upper body arteries 210 before descending to the abdominal aorta (not shown). As mentioned above, the expandable valves of the present invention can be delivered into proximity of the aortic annulus 206 in several ways, including through the patient's vasculature as shown.

In particular, a valve delivery catheter 212 is shown in the cutaway portion of the ascending aorta 204, having been introduced along the direction of the arrow 214 so that a distal end thereof lies adjacent the aortic annulus 206. The catheter 212 can be introduced percutaneously into the patient's arterial system (e.g. into a peripheral artery such as the femoral artery) and advanced to the ascending aorta 204. The catheter shaft preferably has a length of at least about 80 cm, usually about 90-100 cm, to allow transluminal positioning of the shaft from the femoral and iliac arteries to the ascending aorta. Alternatively, the shaft may have a shorter length, e.g. 20-60 cm, for introduction through the iliac artery, through the brachial artery, through the carotid or subclavian arteries, or through a penetration in the aorta itself. In the femoral approach, the catheter is long enough and flexible enough to traverse the path through the femoral artery, iliac artery, descending aorta and aortic arch. At the same time, the catheter has sufficient pushability to be advanced to the ascending aorta by pushing on the proximal end, and has sufficient axial, bending, and torsional stiffness to allow the physician to control the position of the distal end, even when the catheter is in a tortuous vascular structure. Alternatively, the catheter 212 may be passed through a port between ribs in the patient's thorax above the heart and through an incision in the aortic arch 208, in a so-called minimally-invasive procedure.

Techniques for introducing catheters into the human vasculature are well-known, and typically involve the introduction of a guidewire 216 first, followed by an obturator or dilator (not shown) within a sheath 218. The dilator facilitates introduction of the catheter sheath 218 into the vasculature, and is then removed, though the guidewire 216 typically remains in place. Subsequently, a valve of the present invention, such as valve 100 seen in FIGS. 6-15, is delivered over the guidewire 216 and to the distal end of the sheath 218. In accordance with one aspect of the present invention, the valve 100 includes a balloon-expandable portion and thus is mounted over an expansion balloon 222. To facilitate passage of the valve 100 through the sheath 218, a pusher 224 may be used.

Figure 16B:
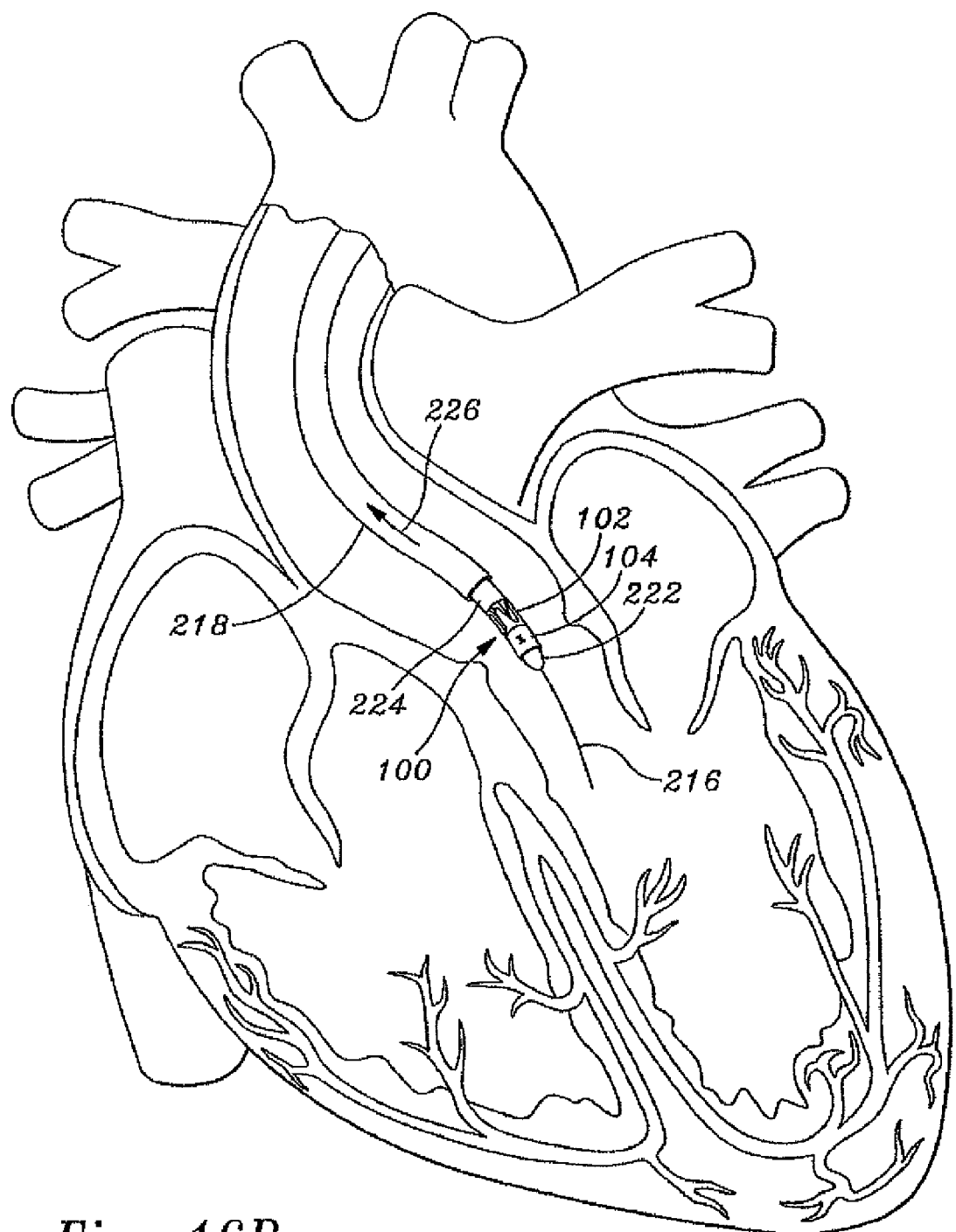

FIG. 16B illustrates a second step in the exemplary valve delivery procedure in which the sheath 218 is retracted in a proximal direction as indicated by arrow 226. Retraction of the sheath 218 exposes the valve 100, which is positioned within the aortic annulus 206 with the assistance of fluoroscopy and radiopaque markers, ultrasonic imaging, or the like.

If the valve 100 includes self-expanding components, retraction of the sheath 218 releases the outer restraint on the valve and permits it to expand into contact with the annulus 206. In the illustrated embodiment, however, the tubular member 140 of the tissue-engaging base 104 is plastically-deformable and retains its radially constricted configuration after retraction of the sheath 218. Because of the rigid connections between the leaflet subassembly 102 and the base 104, the subassembly also remains in its constricted configuration.

Figure 16C:
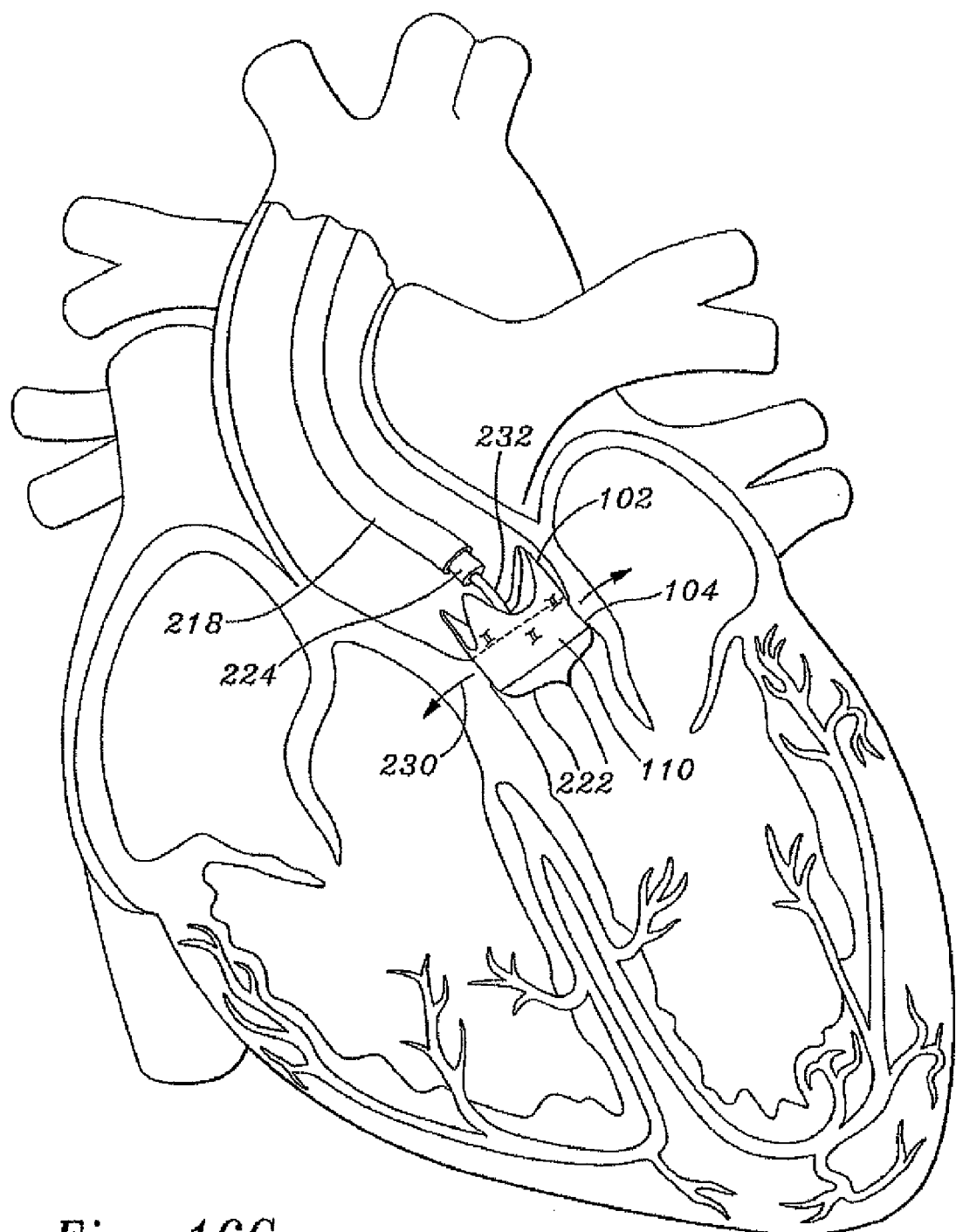

Finally, in FIG. 16C, the balloon 222 is inflated to cause the tissue-engaging base 104 to radially expand into contact with the aortic annulus 206, as indicated by the arrows 230. Simultaneously, the leaflet subassembly 102 radially expands by virtue of the rigid connection with the base 104, and by virtue of its spring bias. A balloon inflation catheter 232 is seen projecting from the pusher 224 and through the leaflet subassembly 102. With reference back to FIG. 6, the fabric skirt 110 is captured between the tubular member 140 and the surrounding tissue, and is in direct contact therewith. Therefore, by virtue of the continuous connection between the cusp edges 124 of the leaflets 108 and the fabric skirt 110, the skirt forms a flow channel for blood entering the inflow end 120 of the valve 100. Again, the plastically-expandable tubular member 140 may be slightly over-expanded to account for any spring-back in the material. Further, as mentioned above, the tubular member 140 may include staples or barbs or other such attachment structure for securely locating the valve 100 within the annulus 206.

Once the valve 100 is fully expanded and securely attached to the annulus 206, the balloon 222 is deflated and removed. Such an operation may include elongating the balloon 222 in the distal direction and reducing its radial dimension by, for example, twisting. Care must be taken so as not to damage the leaflets within the subassembly 102 during retraction of the balloon 222 therethrough. After the balloon 222 has been retracted within the sheath 218, the entire catheter 212 is removed from the patient.

The fully formed valve 100 has a number of distinct advantages over prior expandable valves. For example, as mentioned above, the prosthetic leaflets 108 may be stored in the final, uncompressed implantation shape. This is in contrast to prior expandable valves where the entire valve may be initially compressed such that the leaflets are stored in a compressed state. Consequently, valves of the prior art can be stored for years prior to use, and permanent wrinkling of the compressed leaflets may be a real problem.

Furthermore, each of the leaflets 108 is supported substantially entirely around the undulating wireform 106, which has proven to provide optimal valve performance. Also, separate leaflets are used as opposed to a continuous tube, as in the first embodiment. Additionally, the advantageous low-stress attachment structure of the leaflet tabs 130 to the wireform commissures 112 further increases the durability of the valve.

While the foregoing is a complete description of the preferred embodiments of the invention, various alternatives, modifications, and equivalents may be used. Moreover, it will be obvious that certain other modifications may be practiced within the scope of the appended claims.

What is claimed is:

1. A prosthetic heart valve for delivery into a heart without requiring open heart surgery, comprising:
    a collapsible, self-expanding support stent comprising a shape memory material, the support stent including a generally tubular base along an inflow end and three commissure posts provided along an outflow end and extending in an outflow direction, the three commissure posts being cantilevered from the base, each commissure post having a slot formed therein; and
    a flexible tubular member attached to the support stent, the flexible tubular member comprising a fabric section connected to the base along the inflow end of the support stent and a leaflet section defining three leaflets connected to the commissure posts along the outflow end of the support stent, wherein portions of the leaflet section extend outward through the slots in the commissure posts for securing the leaflet section to the commissure posts;
    wherein the prosthetic heart valve is compressible to a size suitable for delivery into the heart within a catheter and wherein the base of the support stent is expandable to engage the prosthetic heart valve to an annulus of a native aortic valve and wherein the commissure posts of the support stent support the three leaflets downstream of the base, and
    wherein the leaflet section forms loops that pass through each of the commissure posts slots and the prosthetic heart valve further includes inserts disposed within the loops on an outside region of each commissure post, the inserts each having a greater width than the circumferential width of the slots to prevent the loops from pulling inward through the slots.

2. The prosthetic heart valve of claim 1, further including stitches securing the leaflet section loops to the inserts.

3. The prosthetic heart valve of claim 2, further including stitching attaching each insert to a respective commissure post.

4. The prosthetic heart valve of claim 1, wherein the support stent further comprises flanges for improved attachment to host tissue.

5. The prosthetic heart valve of claim 1, wherein the leaflet section is made of bovine pericardial tissue.

6. The prosthetic heart valve of claim 1, wherein the fabric section is attached to the base by sutures.

7. The prosthetic heart valve of claim 1, wherein the fabric section is attached to the leaflet section by sutures along a seam.

8. The prosthetic heart valve of claim 1, wherein the seam is located substantially along an outflow portion of the base.

9. The prosthetic heart valve of claim 1, wherein the fabric section surrounds the base.

10. The prosthetic heart valve of claim 1, wherein the fabric section is made from a polyester material.

11. The prosthetic heart valve of claim 1, wherein the stent further comprises an attachment mechanism configured for securing the valve within the annulus.

12. The prosthetic heart valve of claim 11, wherein the attachment mechanism comprises barbs.

13. The prosthetic heart valve of claim 1, wherein the fabric section comprises polyethylene terephthalate.

14. A prosthetic heart valve for delivery into a heart without requiring open heart surgery, comprising:
    a collapsible, self-expanding support stent comprising a shape memory material, the support stent including a generally tubular base along an inflow end and three commissure posts provided along an outflow end and extending in an outflow direction, the commissure posts being spaced in 120 degree intervals with gaps therebetween, the tubular base comprising a mesh or web, the support stent further comprising at least one attachment member for improved attachment to host tissue;
    a fabric section connected to the base along the inflow end of the support stent, the fabric section made from a polyester material; and a leaflet section directly attached to the fabric section at a seam, the leaflet section defining three leaflets formed of bovine pericardium, the three leaflets attached to the commissure posts for opening and closing;

wherein the prosthetic heart valve is compressible to a size suitable for delivery into the heart within a catheter and wherein the base of the support stent is expandable to engage the prosthetic heart valve to an annulus of a native aortic valve and wherein the commissure posts of the support stent are configured to maintain the three leaflets at a location downstream of the annulus of the native aortic valve, wherein each commissure post has a slot formed therein and wherein portions of the leaflet section pass through the slot in each of the commissure posts for securement to the outside thereof, and wherein the portions of the leaflet section form loops and wherein inserts are disposed within the loops on the outside of each commissure post, the inserts each having a greater width than a circumferential width of the slots to prevent the loops from pulling inward through the slots.

* * * * *